US011480342B2

(12) United States Patent
Kang et al.

(10) Patent No.: US 11,480,342 B2
(45) Date of Patent: Oct. 25, 2022

(54) AIR PURIFIER

(71) Applicant: GUANGDONG ARCAIR APPLIANCE CO., LTD., Guangdong (CN)

(72) Inventors: Zuotian Kang, Guangdong (CN); Haisheng Liang, Guangdong (CN)

(*) Notice: Subject to any disclaimer, the term of this patent is extended or adjusted under 35 U.S.C. 154(b) by 220 days.

(21) Appl. No.: 16/758,383

(22) PCT Filed: Mar. 13, 2019

(86) PCT No.: PCT/CN2019/077911
§ 371 (c)(1),
(2) Date: Apr. 22, 2020

(87) PCT Pub. No.: WO2020/001068
PCT Pub. Date: Jan. 2, 2020

(65) Prior Publication Data
US 2020/0340680 A1 Oct. 29, 2020

(30) Foreign Application Priority Data

Jun. 28, 2018 (CN) ......................... 201810685762.8
Jun. 28, 2018 (CN) ......................... 201821018144.X

(51) Int. Cl.
*A61L 9/00* (2006.01)
*B01D 50/00* (2022.01)
(Continued)

(52) U.S. Cl.
CPC .......... *F24C 15/2035* (2013.01); *A61L 9/014* (2013.01); *A61L 9/015* (2013.01);
(Continued)

(58) Field of Classification Search
CPC .......... A61L 9/015; A61L 9/122; A61L 9/014; B01D 50/00; B01D 53/14
See application file for complete search history.

(56) References Cited

U.S. PATENT DOCUMENTS

| 2,345,798 | A | * | 4/1944 | Daily ...................... C01B 13/11 |
| | | | | 422/186.2 |
| 6,235,090 | B1 | | 5/2001 | Bernstein et al. |
| 10,933,159 | B2 | * | 3/2021 | Benedek ............ B01D 53/8675 |

FOREIGN PATENT DOCUMENTS

| CN | 105730193 A | * | 7/2016 | ............... B60H 3/00 |
| CN | 205561027 U | | 9/2016 | |

(Continued)

OTHER PUBLICATIONS

International search report of PCT/CN2019/077911, dated May 31, 2019.

*Primary Examiner* — Robert A Hopkins

(57) ABSTRACT

An air purifier (100) includes a housing (400) formed with an air duct (401), an ozone generation device (20), an activated carbon purification unit (80), and a fan (200) arranged in the air duct (401). The air duct (401) includes an air inlet (402) and an air outlet (403). The air outlet (403) is disposed indoors. The ozone generation device (20) and the activated carbon purification unit (80) are arranged in the air duct (401) along the direction of the air inlet to the air outlet (403), and the ozone generation device (20) is used to generate ozone. The fan (200) is used to suck gas from the air inlet (402) during operation and let the gas pass through the ozone generation device (20) and the activated carbon purification unit (80) to be discharged from the air outlet (403) into the room.

9 Claims, 11 Drawing Sheets

(51) Int. Cl.
  B01D 53/14      (2006.01)
  F24C 15/20     (2006.01)
  A61L 9/014     (2006.01)
  A61L 9/04      (2006.01)
  A61L 9/12      (2006.01)
  B01D 46/00     (2022.01)
  B01D 46/10     (2006.01)
  C01B 13/11     (2006.01)
  A61L 9/015     (2006.01)
  A61L 101/02    (2006.01)

(52) U.S. Cl.
  CPC ............ *A61L 9/046* (2013.01); *A61L 9/122* (2013.01); *B01D 46/0005* (2013.01); *B01D 46/0028* (2013.01); *B01D 46/0036* (2013.01); *B01D 46/0038* (2013.01); *B01D 46/0043* (2013.01); *B01D 46/10* (2013.01); *B01D 50/00* (2013.01); *B01D 53/14* (2013.01); *C01B 13/115* (2013.01); *A61L 2101/02* (2020.08); *A61L 2209/14* (2013.01); *A61L 2209/212* (2013.01); *B01D 2273/30* (2013.01); *B01D 2279/35* (2013.01); *C01B 2201/12* (2013.01); *C01B 2201/62* (2013.01)

(56) References Cited

FOREIGN PATENT DOCUMENTS

| | | | |
|---|---|---|---|
| CN | 205717818 U | 11/2016 | |
| CN | 206778051 U | * 12/2017 | ............ B01D 46/00 |
| CN | 206778161 U | 12/2017 | |
| CN | 108046215 A | 5/2018 | |
| CN | 208475416 U | 2/2019 | |
| CN | 208536081 U | 2/2019 | |
| CN | 208536083 U | 2/2019 | |
| CN | 208606239 U | 3/2019 | |

* cited by examiner

AIR PURIFIER

CROSS REFERENCE TO RELATED APPLICATION

This application claims priority and rights of patent applications filed with the State Intellectual Property Office of China on Jun. 28, 2018, with patent application numbers of 201810685762.8 and 201821018144.X, and the entire contents of which are incorporated herein by reference.

TECHNICAL FIELD

The application relates to the technical field of air purification, in particular to an air purifier.

BACKGROUND

In the related art, the lampblack generated in the kitchen is sucked by the kitchen ventilator and discharged to the outdoors, so that the gas like lampblack can be prevented from damaging the health of the body. However, in the related art, the purification effect of the kitchen ventilator to discharge the lampblack is poor.

SUMMARY

The object of the application is to solve at least one of the technical problems existing in the prior art. For this purpose, the present application provides an air purifier.

An air purifier provided by the present application, comprising: a housing formed with an air duct, the air duct including an air inlet and an air outlet, and the air outlet is disposed indoors; an ozone generation device and an activated carbon purification unit, the ozone generation device and the activated carbon purification unit being provided in the air duct along a direction from the air inlet to the air outlet, the ozone generation device for generating ozone; and a fan provided in the air duct, the fan is configured for sucking air from the air inlet during operation and allowing the air to pass through the ozone generation device and the activated carbon purification unit to be discharged from the air outlet into a room.

In some embodiments, the exhaust direction of the air outlet is directed upward; or the exhaust direction of the air outlet is toward a side that the air purifier is located; or the purified air is discharged into a cupboard by the air outlet.

In some embodiments, the air purifier includes an air purification module disposed above the fan, the air purification module includes a purification housing, the ozone generation device, and the activated carbon purification unit; wherein the purification housing is formed with a purification air duct, the purification air duct is formed with a purification air inlet and a purification air outlet, the housing includes the purification housing, and the air duct includes the purification air duct, the ozone generation device and the activated carbon purification unit are both disposed in the purification air duct.

In some embodiments, the activated carbon purification unit includes an activated carbon module, the activated carbon module is formed with a plurality of filter holes communicating with the purification air inlet and the purification air outlet, and the plurality of filter holes are arranged in an array.

In some embodiments, the purification housing includes: a cylinder, a lower cover element provided at a lower end of the cylinder, the lower cover element being formed with a lower grille structure communicating with the purification air duct; and an upper cover element provided at an upper end of the cylinder, the upper cover element includes an upper cover plate and an upper mounting ring extending from the upper cover plate in a direction away from the cylinder, the upper cover plate is formed with an upper grille structure communicating with the purification air duct, the upper mounting ring surrounds the upper grille structure to form the purification air outlet, and the activated carbon purification unit is disposed in the upper mounting ring.

In some embodiments, the activated carbon purification unit includes a fixed ring, the activated carbon module is fixed in the fixing ring, and the activated carbon purification unit is fixed in the upper mounting ring through the fixing ring.

In some embodiments, the lower cover element includes a lower cover plate and a lower mounting ring extending from the lower cover plate in a direction away from the cylinder, the lower cover plate is formed with the lower grille structure, and the lower mounting ring surrounds the lower grille structure to form the purification air inlet.

In some embodiments, the ozone generation device includes: a frame and multi-turn coils are wound around the frame, wherein the multi-turn coils are arranged at intervals, at least two turns of the coils are used to ionize air to form ozone after an operating voltage is applied.

In some embodiments, the frame includes: two polar plates, wherein the two plates are set opposite to each other and at intervals; and a plurality of connection posts connected to the two polar plates and arranged at intervals, and the multi-turn coils are wound around the plurality of connection posts and arranged at intervals along an axial direction of the connection posts.

In some embodiments, coils to which a low potential is applied and coils to which a high potential is applied are alternately distributed in the arrangement direction of the multi-turn coils, wherein the low potential is 0V and the high potential is 3000-3500V.

The air purifier according to the embodiment of the application purifies the air through the ozone generation device and the activated carbon purification unit, so that the air purifier has better air purification capacity, so that the purified lampblack gas can be discharged directly to the room, which not only has the effect of purifying lampblack gas, but also is conducive to indoor air circulation, environmental protection and energy conservation.

Part of additional aspects and advantages of the present application will be given in the following description, part of which will become apparent from the following description, or be learned through practice of the present application.

BRIEF DESCRIPTION OF THE DRAWINGS

The above and/or additional aspects and advantages of the present application will become apparent and easily understood from the description of the embodiments in conjunction with the following drawings, wherein.

Figure 1:
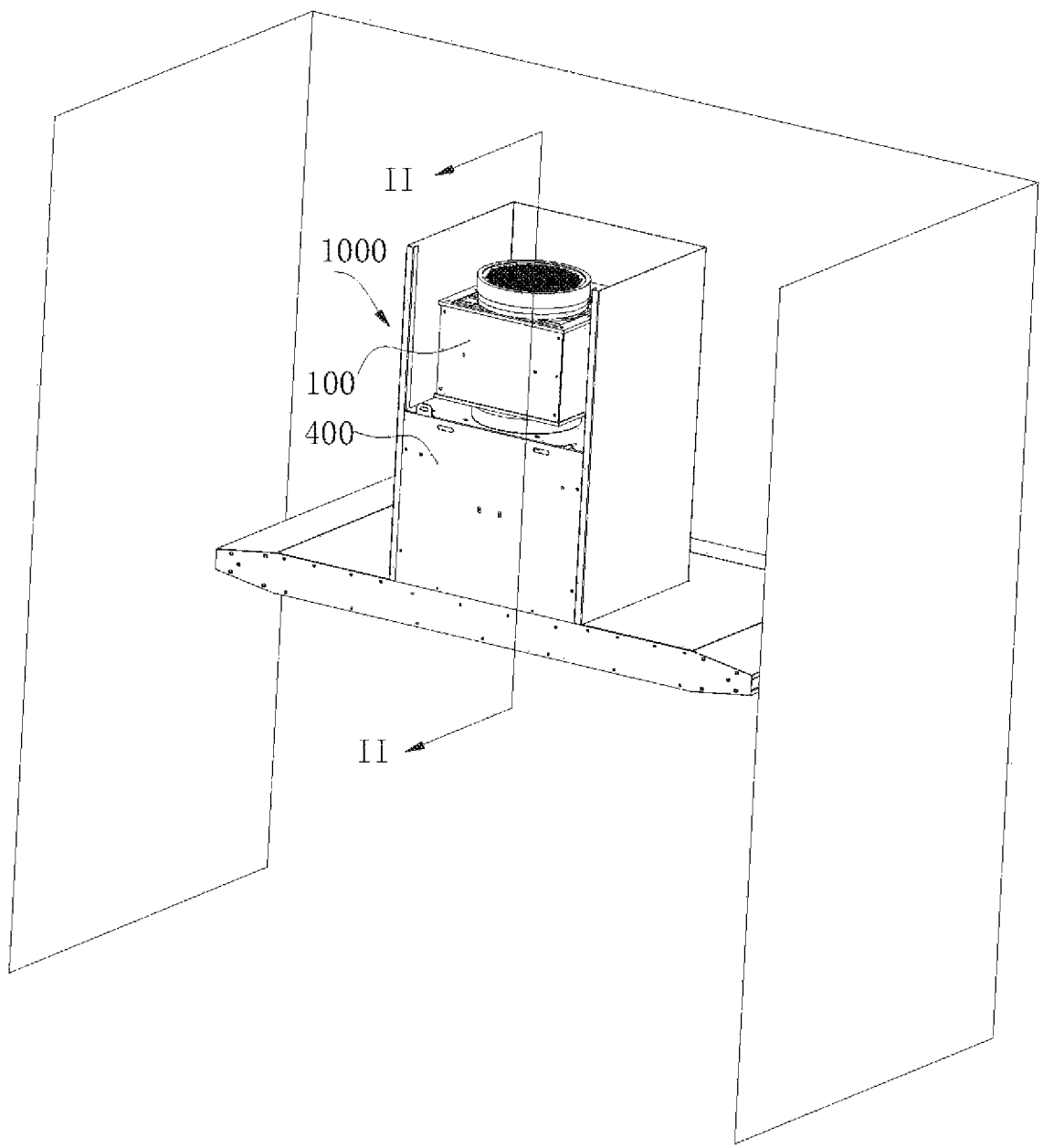
FIG. 1 is a schematic perspective view of an air purifier according to an embodiment of the present application.

Explanation of main component symbols are shown as below:

Air purifier 1000, air purification module 100, purification housing 10, cylinder 11, purification air duct 12, purification air inlet 122, purification air outlet 124, upper cover element 14, upper cover plate 141, upper grille structure 1412, upper mounting ring 144, lower cover element 16, lower cover plate 161, lower grille structure 1612, lower mounting ring 164, ozone generation device 20, frame 22, connection plate 222, connection post 224, coil 24, high voltage transformer 50, switch 60, button 62, switch box cover 70, activated carbon purification unit 80, activated carbon module 802, filter hole 8022, fixing ring 804, fan 200, power socket 300, housing 400, air duct 401, air inlet 402, air outlet 403, power supply device 500, length A, width B, distance C, thickness D, diameter E, cross-sectional area S, and center distance F.

DETAILED DESCRIPTION OF THE EMBODIMENTS

The embodiments of the present application are described in detail below, and examples of the embodiments are shown in the drawings, wherein the same or similar reference numerals indicate the same or similar elements or elements having the same or similar functions throughout. The embodiments described below with reference to the drawings are exemplary and are only used to explain the present application, and should not be regarded as limitation on the present application.

In the description of the application, it should be understood that the terms indicating the positional or orientation relationship are based on the orientation or positional relationship shown in the drawings, such as "center", "longitudinal", "transverse", "length", "width", "thickness", "upper", "lower", "front", "rear", "left", "right", "vertical", "horizontal", "top", "bottom", "inside", "outside", "clockwise", "counterclockwise", etc., and the terms are only for the convenience of describing this application and simplifying the description, not indicating or implying that the device or element referred to must have a specific orientation, structure and operation in a specific orientation. Therefore, it cannot be understood as a limitation on the application. In addition, the terms "first" and "second" are used for descriptive purposes only and cannot be understood as indicating or implying relative importance or implicitly indicating the number of technical features indicated. Therefore, the features defined as "first" and "second" may explicitly or implicitly include one or more of the features. In the description of the present application, the meaning of "a plurality" is two or more, unless it is specifically and specifically defined otherwise.

In the description of this application, it should be noted that the terms "installation", "connected", and "connected" should be understood in a broad understanding, unless explicitly stated and limited otherwise. For example, it may be fixed connections or removable, or integrated, or mechanical connection; it can be electrical connection, or can communicate with each other, it can be can be directly connected, or it can be indirectly connected through an intermediate medium, it can be the internal communication of two elements or the interaction of two elements relationship. For those of ordinary skill in the art, the specific meanings of the above terms in this application can be understood according to specific situations.

In the application, unless explicitly stated and limited otherwise, the "on" or "under" of the second feature may include the first and second features in direct contact, and may also include the first and second features not directly contact, but through another features contact between them. Moreover, the first feature is "above", "upper", and "higher" the second feature, including that the first feature is directly above and obliquely above the second feature, or merely indicating that the first feature is higher in level than the second feature. The first feature is "below", "lower", and "beneath" of the second feature, including that the first feature is directly below and obliquely below the second feature, or merely indicating that the first feature is lower in horizontal than the second feature.

The following disclosure provides many different implementations or examples for implementing different structures of the present application. To simplify the disclosure of this application, the components and settings of specific examples are described below. Of course, they are merely examples and are not intended to limit the application. Furthermore, the present application may repeat reference numbers and/or reference letters in different examples, and such repetition is for the sake of simplicity and clarity, and does not indicate a relationship between the various embodiments and/or settings discussed. In addition, examples of various specific processes and materials are provided in this application, but those of ordinary skill in the art can be aware of the application of other processes and/or the use of other materials.

Figure 2:
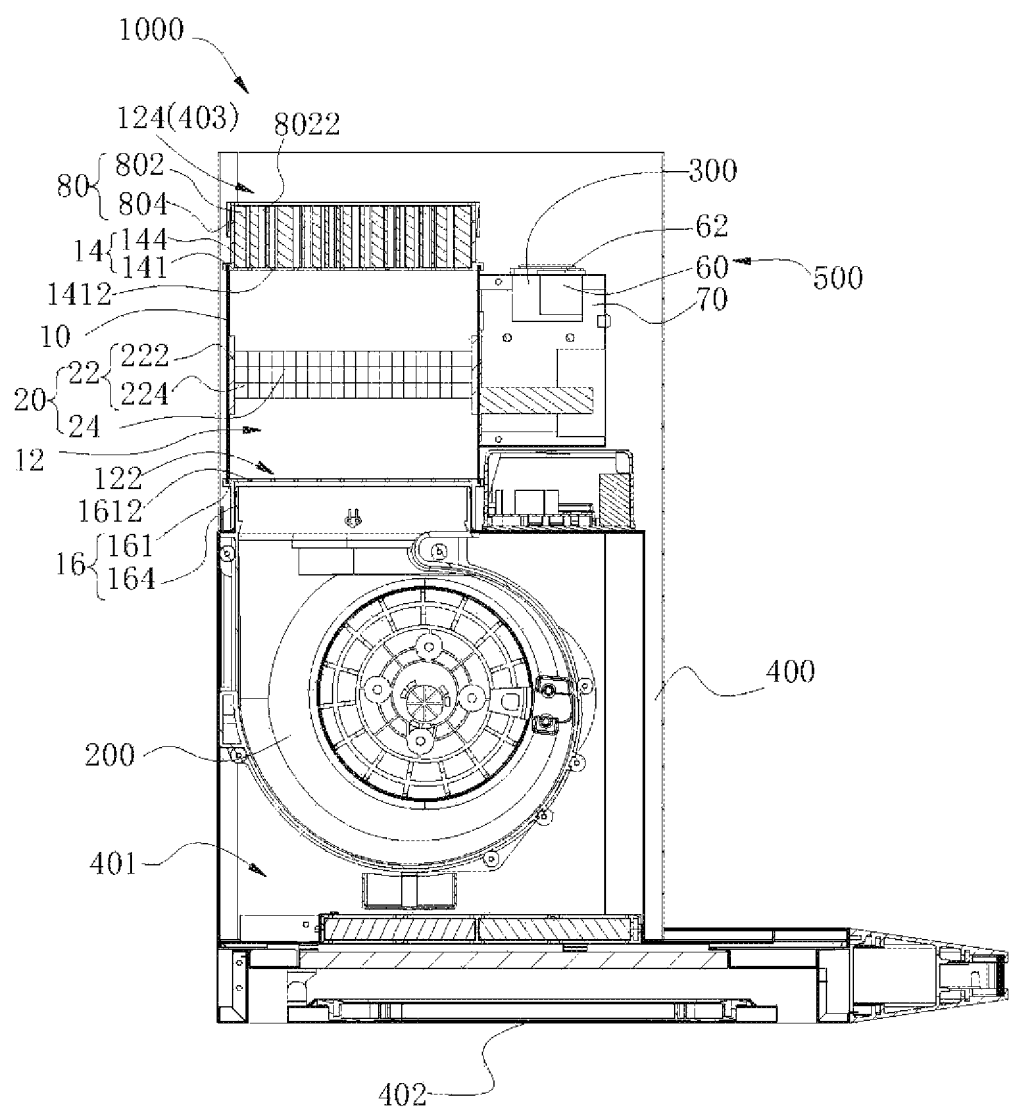
FIG. 2 is a schematic cross-sectional view of the air purifier of FIG. 1 along the II-II direction.

Please refer to FIG. 1 and FIG. 2. The air purifier 1000 according to the embodiment of the application includes an air purification module 100 and a fan 200.

Figure 3:
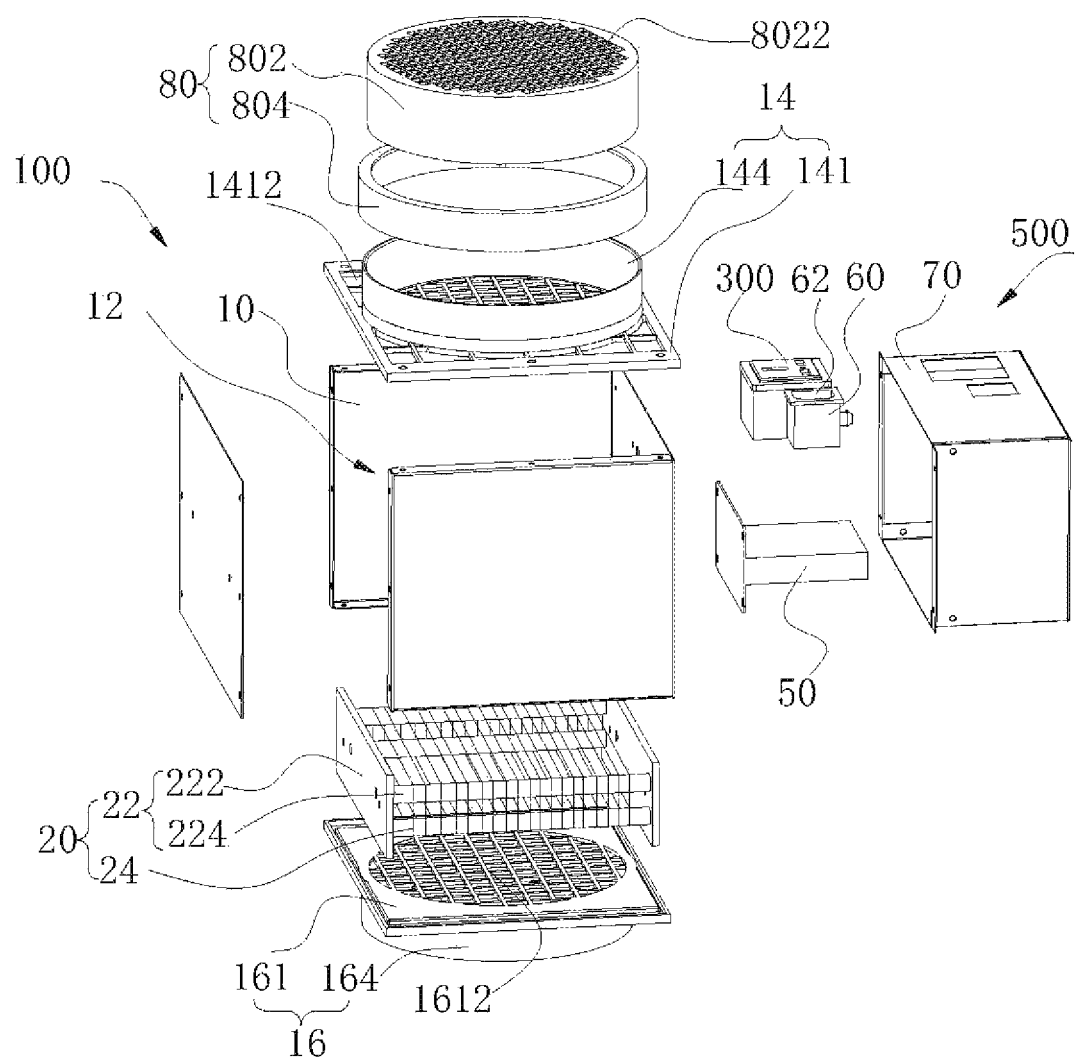
FIG. 3 is an schematic exploded view of an air purification module according to an embodiment of the present application.
Figure 4:
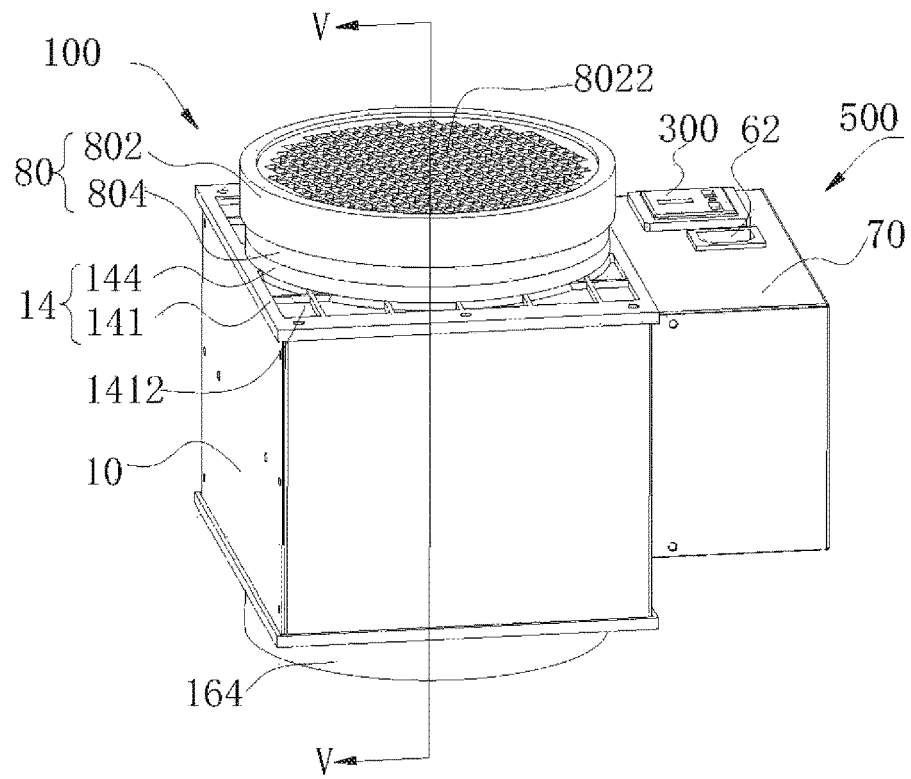
FIG. 4 is a schematic perspective view of the air purification module according to an embodiment of the present application.
Figure 5:
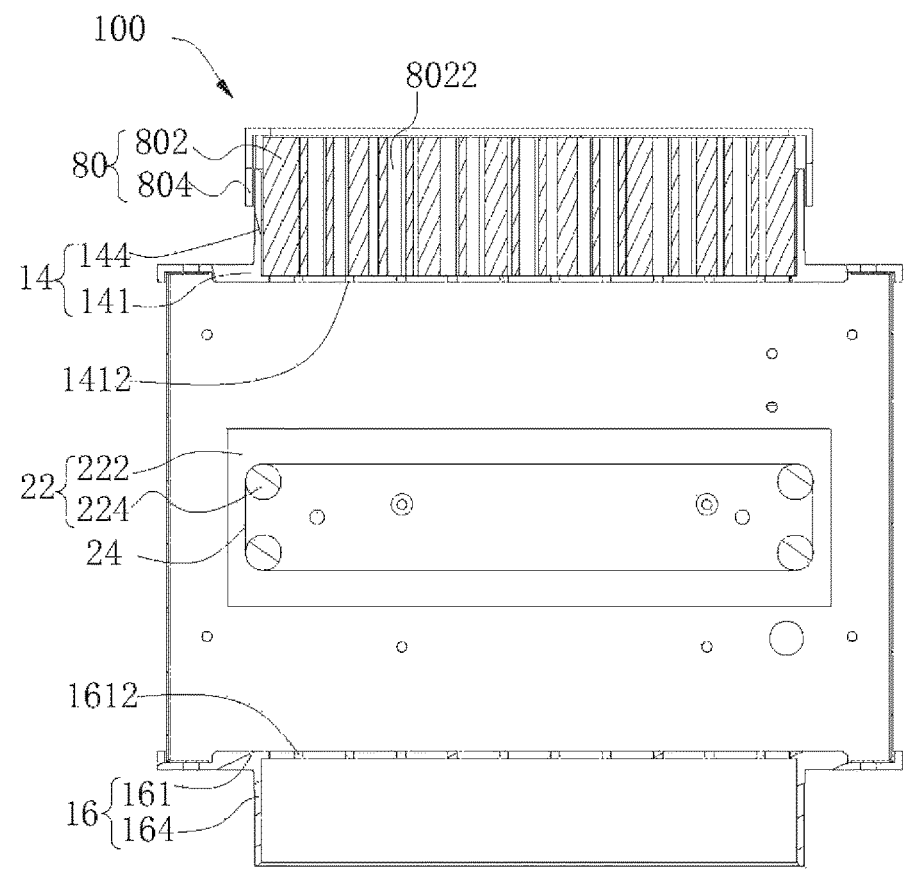
FIG. 5 is a schematic cross-sectional view of the air purifier of FIG. 4 along the V-V direction.

Referring to FIG. 3, FIG. 4 and FIG. 5, the air purification module 100 according to the embodiment of the application includes a purification housing 10 formed with a purification air duct 12, an ozone generation device 20 and an active carbon purification unit 80 that are arranged in the purification air duct. The purification air duct 12 is provided with a purification air inlet 122 and a purification air outlet 124, and the ozone generation device 20 and the activated carbon purification unit 80 are interval setting in sequence along the direction from the purification air inlet 122 to the purification air outlet 124. The activated carbon purification unit 80 includes an activated carbon module 802, which is provided with a plurality of filter holes 8022. The plurality of filter holes 8022 are communicated with the purification air inlet 122 and the purification air outlet 124, and the plurality of filter holes 8022 are arranged in an array. The fan 200 is configured for sucking air and discharging the air to purification air duct 12.

The air purification module 100 according to the embodiment of the present application is provided with an activated carbon purification unit 80, so that the structure of the air purification module 100 is simple, and the odor removal and air purification effects are better.

Activated carbon is a very small carbon particle with a large surface area. Therefore, the activated carbon can fully contact the air. In addition, the carbon particles have smaller pores-capillaries. The capillary has a strong adsorption capacity, and impurities in the air will be adsorbed when it hits the capillary, so that the air is purified. The activated carbon adsorption method is widely used, the technology is mature, safe and reliable, and it can adsorbed various types of substances. The installation of the activated carbon purification unit 80 in the air purification module 100 is simple and convenient, and is beneficial to further purify the air and remove odors.

The purification housing 10 of the air purification module 100 has a substantially rectangular tube shape. In this way, while making the air purifier 1000 more beautiful in appearance, the structure of the air purifier 1000 can be made more compact, which is beneficial to miniaturization of the air purifier 1000. It can be understood that, in other embodiments, the purification housing 10 may have other shapes such as a cylindrical shape, a polygonal cylindrical shape, and the like. In addition, the purification housing 10 and the fan case may be made of plastic.

Figure 6:
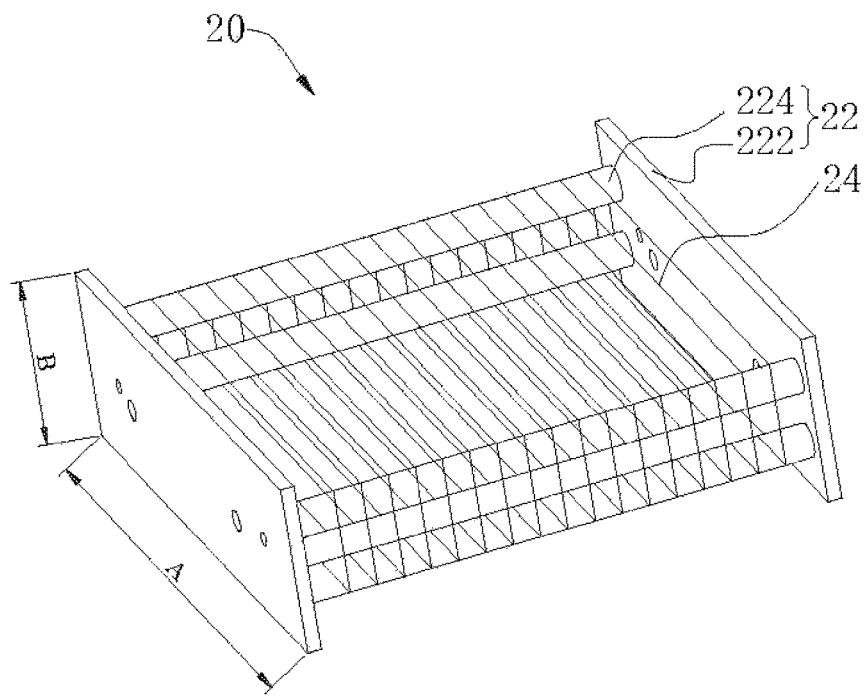
FIG. 6 is a schematic perspective view of an ozone generation device according to an embodiment of the present application.

Please refer to FIG. 6. The ozone generation device 20 includes a frame 22 and multi-turn coils 24 arranged on the frame 22. The multi-turn coils 24 are arranged at intervals. Wherein, an operating voltage is applied between at least two of the coils 24 to ionize air to form ozone.

The air purifier 1000, the air purification module 100, and the ozone generation device 20 according to the embodiment of the present application ionize the air through the coil 24 to form ozone, so that the structure of the ozone generation device 20 is simple, and sufficient ozone can be generated to remove odor.

It can be understood that ozone is a strong oxidant, which can destroy and decompose the cell wall of bacteria, thus ozone can diffuse into the cells and oxidize and decompose the glucose oxidase necessary for bacteria to oxidize glucose. And ozone can has reaction directly with bacteria and virus, so as to destroy the metabolism and reproduction process. In addition, ozone can oxidize various odorous inorganic or organic substances. For example, ozone can decompose odorous gases such as ammonia, benzene, and hydrogen sulfide, thereby deodorizing the air. In summary, the time for ozone sterilization, disinfection and deodorization is short and the effect is strong. Ozone generated from the ionized air by the ozone generation device 20 can remove odor and make a good air purify effect.

Figure 7:
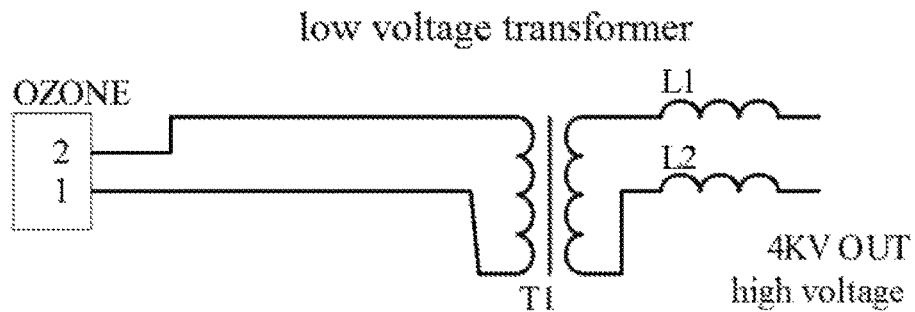
FIGS. 7-9 are schematic circuit diagram for preparing ozone of the ozone generation device according to an embodiment of the present application.
Figure 8:
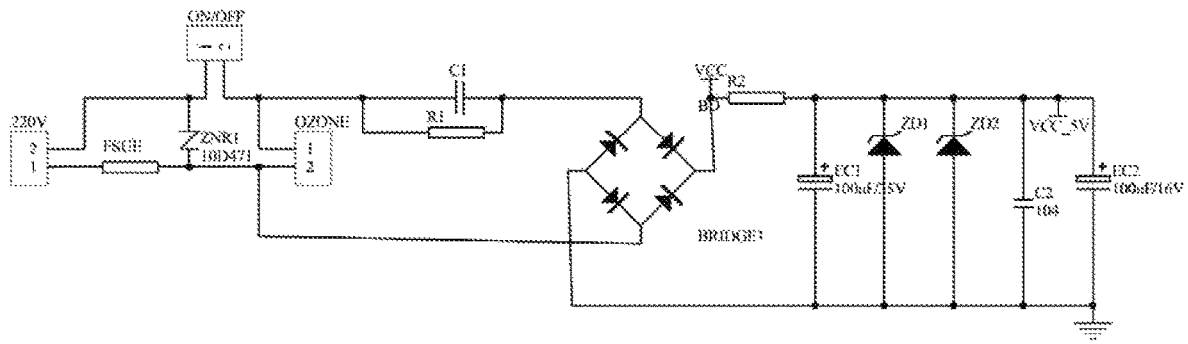
Figure 9:
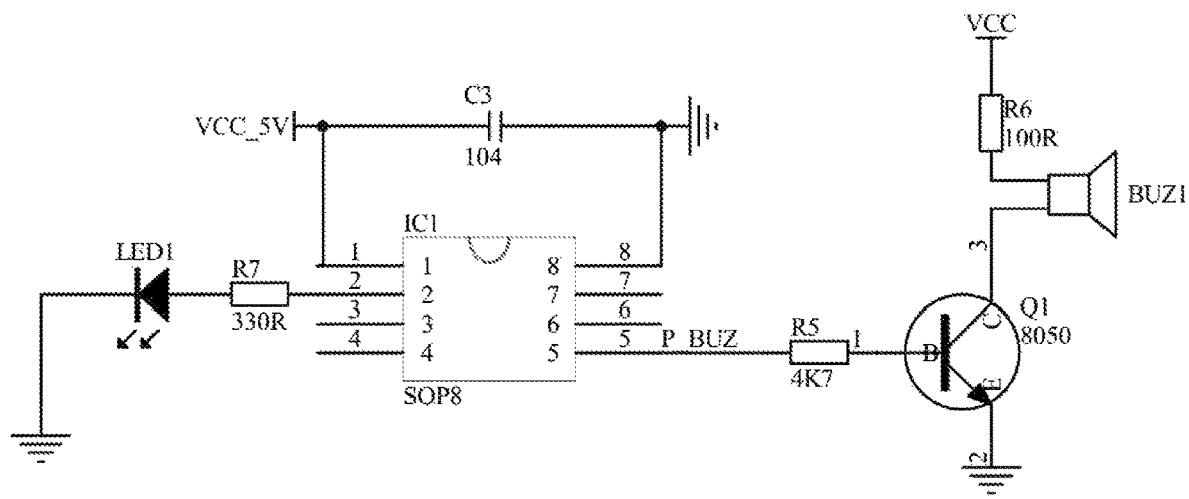

FIG. 7, FIG. 8 and FIG. 9 are schematic circuit diagram for preparing ozone of the ozone generation device 20. The ozone generation device 20 according to the embodiment of the application adopts the corona discharge method to prepare ozone. Specifically, in the ozone generation device 20, the oxygen molecules are excited by electrons to obtain energy and collide with each other elastically to polymerize into ozone molecules. The chemical equation for the formation of ozone by ionizing air of ozone generation device 20 is as follows:

$$3O_2 \rightarrow 2O_3$$

Figure 10:
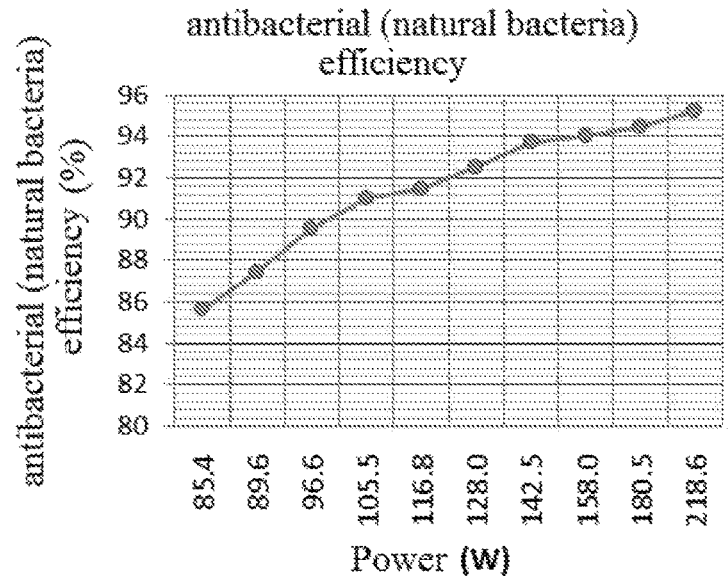
FIG. 10 is a schematic diagram showing the relationship between the sterilization (natural bacteria) efficiency of the air purification module and the ozone generation device according to the embodiment of the present application.

Please refer to FIG. 10 and table 1 below. FIG. 10 is a schematic diagram of the relationship between the sterilization (natural bacteria) efficiency of the air purification module and the ozone generation device 20 according to the embodiment of the application, wherein the horizontal axis is the power of the ozone generation device 20, the unit is Watt (W), the vertical axis is the sterilization (natural bacteria) efficiency, and the unit is percentage (%). Table 1 is the analysis and test results of the air purification module 100 according to the embodiment of the application on the antibacterial (sterilization) function of natural bacteria. The results showed that after 24 hours, the antibacterial (natural bacteria) efficiency of ozone generation device 20 was 92.4%, the antibacterial effect is good.

TABLE 1

| | | | | Test results | | | |
|---|---|---|---|---|---|---|---|
| Analysis item | Action time | Test bacteria | Serial number | Bacteria content in air before test in the test group (CFU/m$^3$) | Bacteria content in air after the test in the test group (CFU/m$^3$) | Antibacterial (sterilization) rate (%) | Detection method |
| Antibacterial (sterilization) function | 24 h | Natural bacteria | 1 | 6.43 × 10$^2$ | 49 | 92.4 | "Technical Standard For Disinfection" (2002 Edition 2.1.3 |

Figure 11:
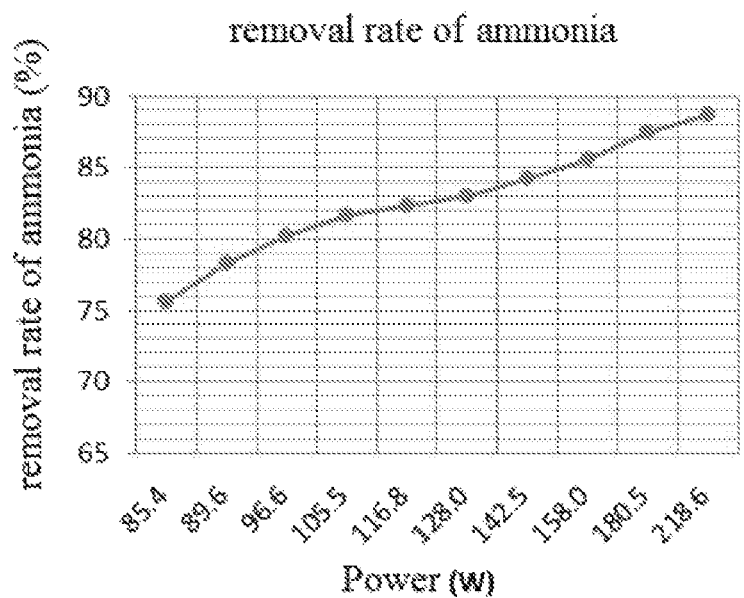
FIG. 11 is a schematic diagram showing a relationship between an ammonia removal rate of the air purification module and the ozone generation device according to an embodiment of the present application.
Figure 12:
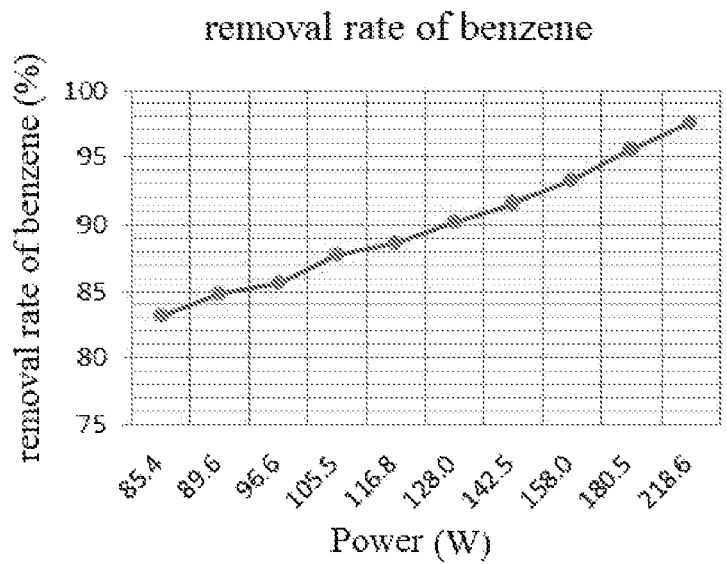
FIG. 12 is a schematic diagram showing a relationship between a benzene removal rate of the air purification module and the ozone generation device according to an embodiment of the present application.

Please refer to FIG. 11, FIG. 12, and Table 2. FIG. 11 is a schematic diagram showing the relationship between the ammonia removal rate of the air purification module and the ozone generation device 20 according to the embodiment of the present application, wherein the horizontal axis is the power of the ozone generation device 20 and the unit is Watt (W), and the vertical axis is the ammonia removal rate and the unit is percentage (%).

FIG. 12 is a schematic diagram showing the relationship between the benzene removal rate of the air purification module and the ozone generation device according to the embodiment of the present application, wherein the horizontal axis is the power of the ozone generation device 20 and the unit is Watt (W), and the vertical axis is the benzene removal rate and the unit is percentage (%).

Table 2 shows the analysis and detection results about ammonia and benzene of the air purification module 100 according to the embodiment of the present application. The test results show that after 24 hours, the removal rate of ammonia by air purification module 100 reaches 88.7%, and the removal rate of benzene reaches 97.6%, and the effect is good.

Figure 13:
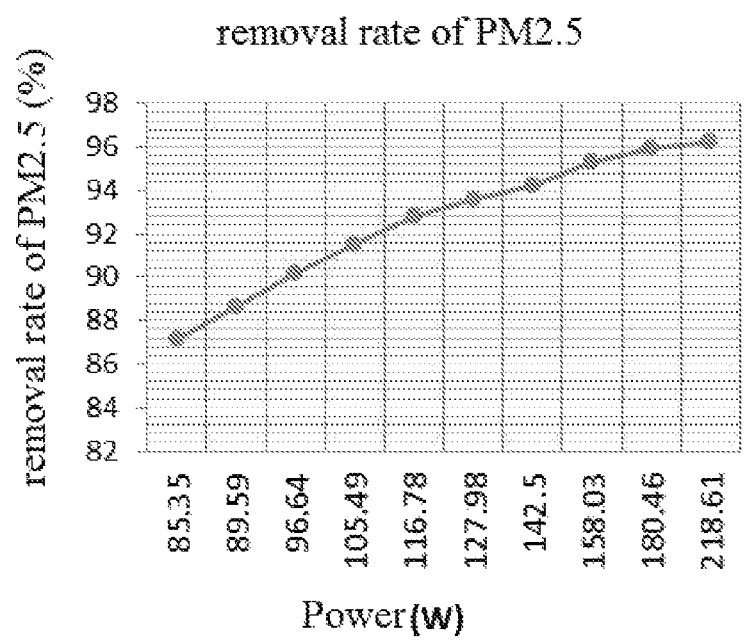
FIG. 13 is a schematic diagram showing a relationship between a PM2.5 removal rate of the air purification module and the ozone generation device according to an embodiment of the present application.

Please refer to FIG. 13 and Table 4. FIG. 13 is a schematic diagram showing the relationship between the PM2.5 removal rate of the air purification module and the ozone generation device 20 according to the embodiment of the present application.

Wherein, the horizontal axis is the power of the ozone generation device 20, the unit is Watt (W), and the vertical axis is the PM2.5 removal rate, the unit is percentage (%). Table 4 shows analysis and detection results about the PM2.5 of the air purification module 100 according to the embodiment of the present application. The detection test shows that the PM2.5 removal rate of the ozone generation device 20 reaches 96.3% within 4 hours, and the effect is good.

TABLE 4

| Analysis item | Test Result | | Removal rate under test conditions (%) | Detection method |
|---|---|---|---|---|
| | concentration that sample is added for 0 h (mg/m$^3$) | concentration that sample is added for 4 h (mg/m$^3$) | | |
| PM2.5 | 6.23 | 0.228 | 96.3 | Refer to APAIC/LM 01-2013 "Indoor air cleaner's purification performance evaluation requirements" |

TABLE 2

| | | Test results | | | |
|---|---|---|---|---|---|
| Analysis item | Action time | Concentration of pollutants in blank test chamber (mg/m$^3$) | Concentration of pollutants in the sample test chamber (mg/m$^3$) | Removal rate (%) | Detection method |
| ammonia | 24 h | 11.54 | 1.30 | 88.7 | QB/T 2761-2006 |
| benzene | | 9.8 | 0.23 | 97.6 | |

Table 3 shows the results of analysis results of the air purification module 100 according to the embodiment of the application on the antibacterial (bactericidal) function of *Staphylococcus albus* 8799. The detection test shows that after 1 hour, the antibacterial (sterilization) rate of the air purification module 100 to *Staphylococcus albus* 8799 is about 95%, and the effect is good.

TABLE 3

| | | | | Test Result | | | | | | |
|---|---|---|---|---|---|---|---|---|---|---|
| Analysis item | Action time | Test bacteria | Serial number | Bacteria content in air before the test in the blank group (CFU/m$^3$) | Bacteria content in air after the test in the blank group (CFU/m$^3$) | Natural death rate (%) | Bacteria content in air before the test in the test group (CFU/m$^3$) | Bacteria content in air after the test in the test group (CFU/m$^3$) | Antibacterial (sterilization) rate (%) | Detection method |
| Antibacterial (sterilization) function | 1 h | *Staphylococcus albus* 8799 | 1 | $8.13 \times 10^4$ | $5.94 \times 10^4$ | 26.9 | $8.24 \times 10^4$ | $2.70 \times 10^3$ | 95.52 | "Technical Standard For Disinfection" (2002 Edition) 2.1.3 |
| | | | 2 | $7.47 \times 10^4$ | $5.31 \times 10^4$ | 28.9 | $7.48 \times 10^4$ | $2.92 \times 10^3$ | 94.51 | |
| | | | 3 | $7.95 \times 10^4$ | $5.66 \times 10^4$ | 2.88 | $7.87 \times 10^4$ | $3.00 \times 10^3$ | 94.65 | |

Table 5 shows the analysis and detection results about the PM2.5 clean air delivery rate of the air purification module 100 according to the embodiment of the present application. The detection test shows that the PM2.5 clean air delivery rate of the ozone generation device 20 reaches 15.5 m³/h, that is to say, the ozone generation device 20 not only has a good removal rate, but also has a high clean air delivery rate.

TABLE 5

| Analysis item | Test results | measurement unit | Detection method |
| --- | --- | --- | --- |
| PM2.5 clean air delivery rate ($CADR_{PM2.5}$) | 15.5 | m³/h | APAIC/LM 01-2013 (Appendix B) |

It can be seen from the above chart, the air purification module 100 according to the embodiment of the present application has a removal rate of 92.4% for natural bacteria, a removal rate of 96.3% for PM2.5, a removal rate of 88.7% for ammonia, and a removal rate of 97.6% for benzene, and a removal rate for *Staphylococcus albicans* is about 95%. That is to say, the detection test shows that the removal rate of the air purification module 100 according to the embodiment of the present application can reach 88% or more for each removal objects to be removed, and the removal rate for most of the objects to be removed can reach about 95%, which has an excellent effect.

In some embodiments, the frame 22 includes two connection plates 222 and a plurality of connection posts 224, and the two connection plates 222 are set opposite to each other and at intervals. The plurality of connection posts 224 are connected to the two connection plates 222 and are arranged at intervals. The multi-turn coils 24 are wound around the plurality of connection posts 224 and is arranged at intervals along the axial direction of the connection posts 224.

In one example, as shown in FIG. 6, there are four connection posts 224 in total; in another example, there are six connection posts 224 in total; in yet another example, there are eight connection posts 224 in total. The number of connection posts 224 is not limited herein.

In some embodiments, two connection plates 222 are insulators. In this way, the two connection plates 222 can shield the electric field generated by the coils, to prevent the electric field from leaking and improve the safety of the ozone generation device 20. Specifically, the connection plate 222 may be made of an insulating material such as acrylic. The two connection plates 222 may be symmetrically distributed about a central axis of the air purification module 100.

Referring to FIG. 6, in some embodiments, each connection plate 222 has a rectangular cross section. The length A of the connection plate 222 is 145-150 mm, and the width B of the connection plate is 150-160 mm.

In addition, the length A of connection plate 222 can be arbitrarily taken in the range of 145-150 mm, and the width B of connection plate 222 can be arbitrarily taken in the range of 150-160 mm.

In one example, the length A of the connection plate 222 is 145 mm and the width B is 150 mm. In another example, the length A of the connection plate 222 is 150 mm and the width B is 160 mm. In yet another example, the length of the connection plate 222 is A is 147 mm and the width B is 155 mm.

In some embodiments, the plurality of connection posts 224 surround a rectangular parallelepiped space, and the multi-turn coils 24 are evenly distributed along the axial direction of the connection posts 224. It can be understood that, because the purification housing 10 is rectangular and the cross section of the connection plate 222 is rectangular, the rectangular parallelepiped space surrounded by the connection posts 224 can be adapted to the purification housing 10 and the connection plate 222, thereby making the air purification module 100 more compact, which is beneficial to the miniaturization of the air purification module 100. Furthermore, the multi-turn coils 24 are evenly distributed along the axial direction of the connection post 224, which is beneficial to the beauty and regularity of the product.

Figure 14:
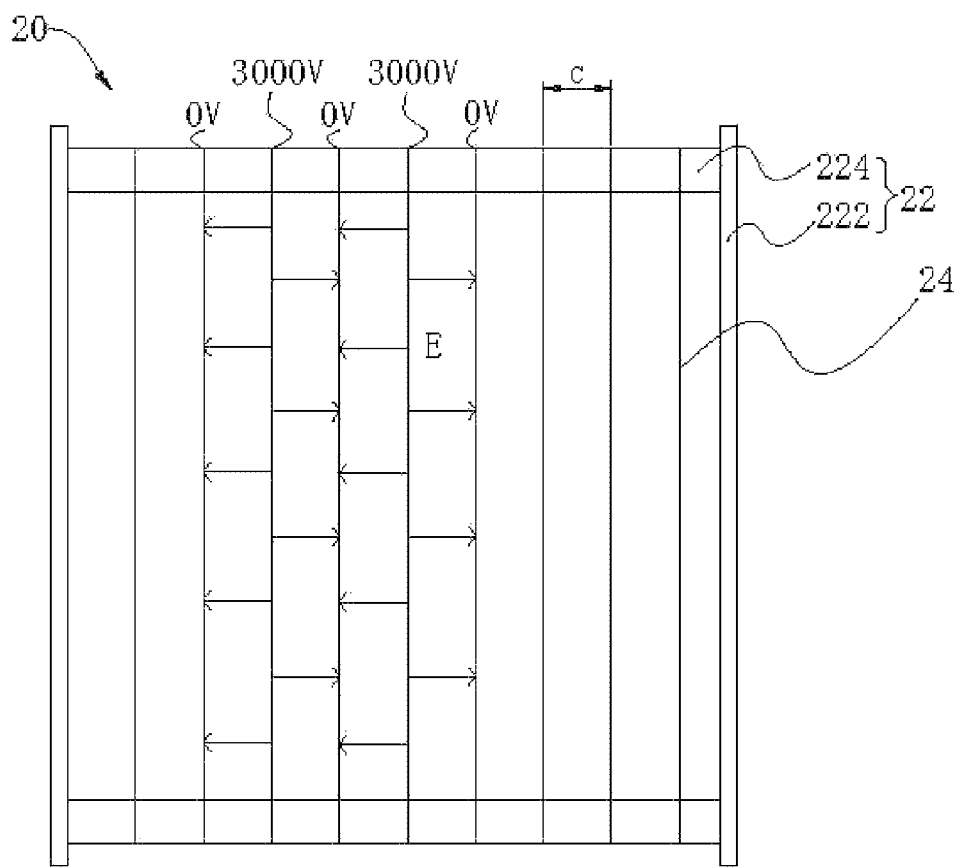
FIGS. 14 to 16 are schematic plan views of the ozone generation device according to an embodiment of the present application.

Referring to FIG. 14, in some embodiments, an operating voltage is applied between any two adjacent turns of the coils 24, and a distance C between the adjacent two turns of the coils is 10-15 mm. That is to say, the distance C between two adjacent turns of the coils can take any value between 10-15 mm.

In one example, the distance C between adjacent two turns of the coils is 10 mm; in another example, the distance C between adjacent two turns of the coils is 15 mm; in yet another example, the interval C between the adjacent two turns of the coils is 12.5 mm.

In one embodiment, in the arrangement direction of the multi-turn coils 24, the coils 24 to which a low potential is applied and the coils 24 to which a high potential is applied are alternately distributed at intervals. Wherein the low potential is 0V and the high potential is 3000-3500V. For example, in the direction of the arrangement of the multi-turn coils 24, the first-turn coil 24 has a low potential (for example, 0V), the second-turn coil 24 has a high potential (for example, 3000V), and the third-turn coil 24 has a low potential . . . such arrangement in order.

Figure 15:
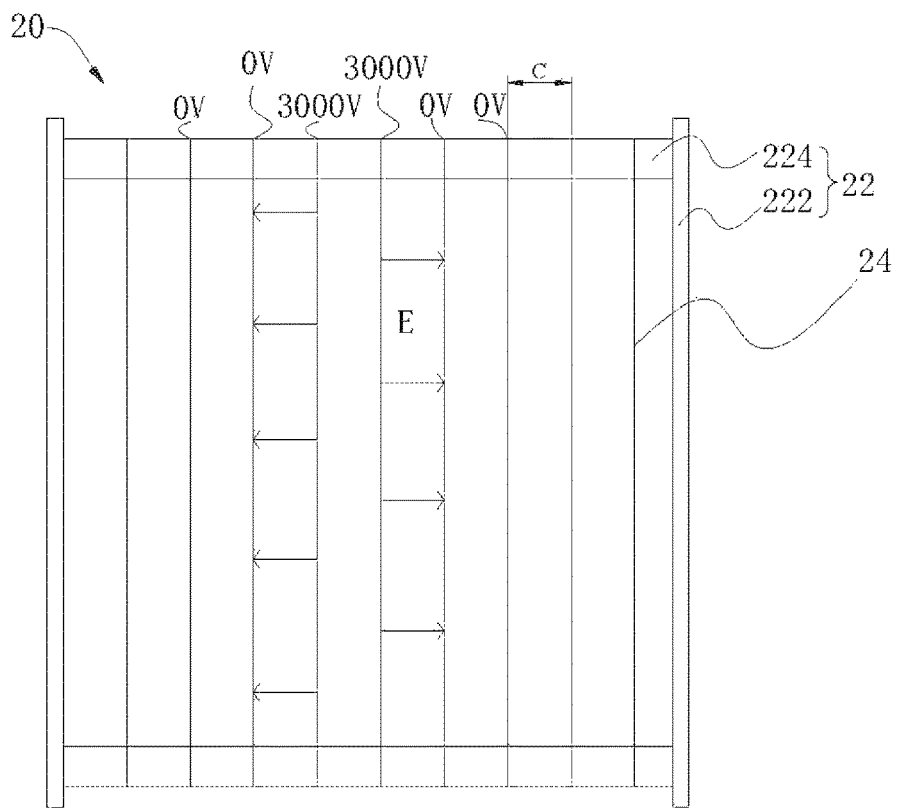

Referring to FIG. 15, in another embodiment, the first-turn coil 24 has a low potential (for example, 0V), the second-turn coil 24 has a low potential (for example, 0V), and the third-turn coil 24 has a high potential (for example, 3000V), the fourth-turn coil 24 has a high potential (for example, 3000V), the fifth-turn coil 24 has a low potential (for example, 0V), the sixth-turn coil 24 has a low potential (for example, 0V), such arrangement in order.

Figure 16:
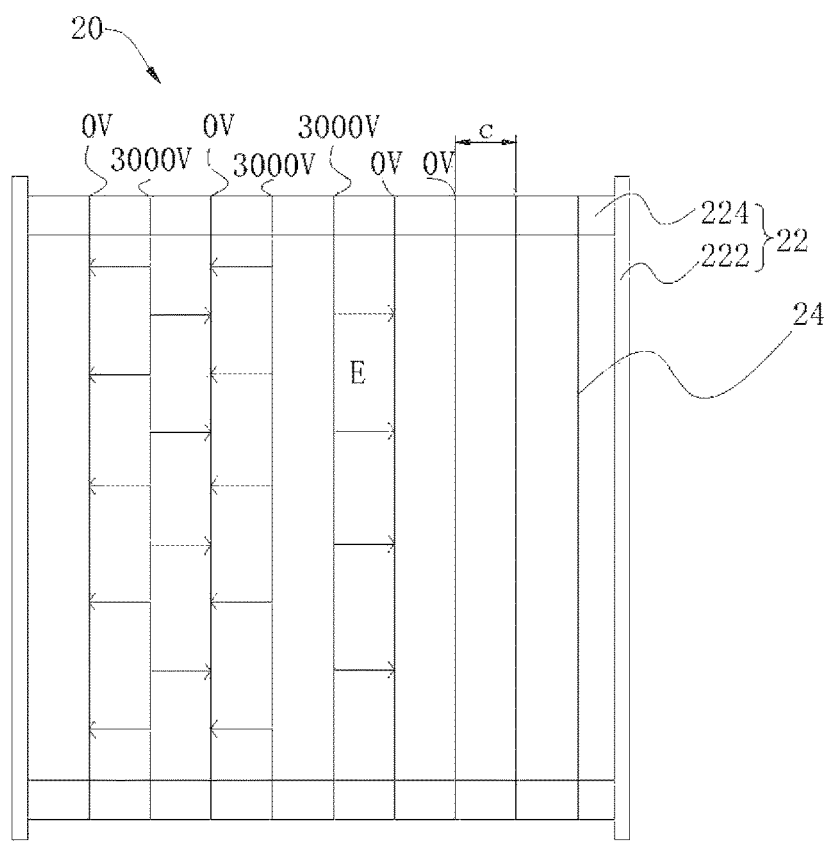

Please note that the above "attributes" such as "first", "second", and "third" represent the relative positional relationship between the coils 24 to which the potential is applied, not the sequence of the coils in all the coils 24. For example, in one example, the coil 24 has a total of 18 turns, the first-turn coil 24 has a low potential (for example, 0V), the second-turn coil 24 has a high potential (for example, 3000V), and the third-turn coil 24 has a low potential (for example, 0V)). The first-turn coil 24 in this example is relative to the second-turn coil 24 and the third-turn coil 24. It can be the first turn of the 18 turn coils, or the second turn of the 18 turn coils. It can also be the third turn of the 18 turn coils. In addition, the "first", "second", "third" and other attributive terms do not mean that the potential-applied coils 24 are adjacent to each other, and there may be a coil 24 to which no potential is applied between them. In addition, as shown in FIG. 16, the application of the potential of the multi-turn coils 24 may be irregular.

In some embodiments, the number of turns of the coil 24 is 15-20 turns. That is to say, the number of turns of the coil 24 can take any value between 15-20 turns. In one example, the number of turns of the coil 24 is 15 turns; in another example, the number of turns of the coil 24 is 20 turns; in yet another example, the number of turns of the coil 24 is 17 turns.

In some embodiments, the operating voltage is 3000-3500V. As mentioned earlier, oxygen can form ozone under the condition of discharge, and when the operating voltage is 3000-3500V, the efficiency of ozone generation can be higher. In one example, the operating voltage is 3000V; in another example, the operating voltage is 3500V; in yet another example, the operating voltage is 3200V.

Figure 17:
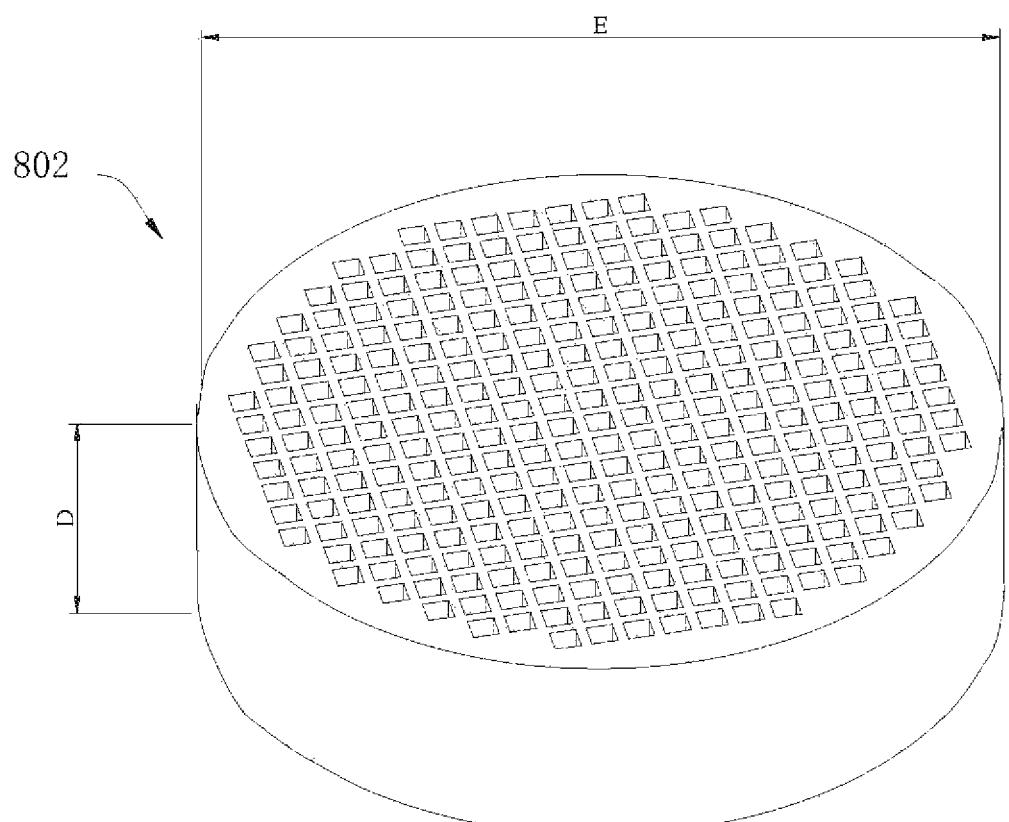
FIG. 17 is a schematic perspective view of an activated carbon module according to an embodiment of the present application.
Figure 18:
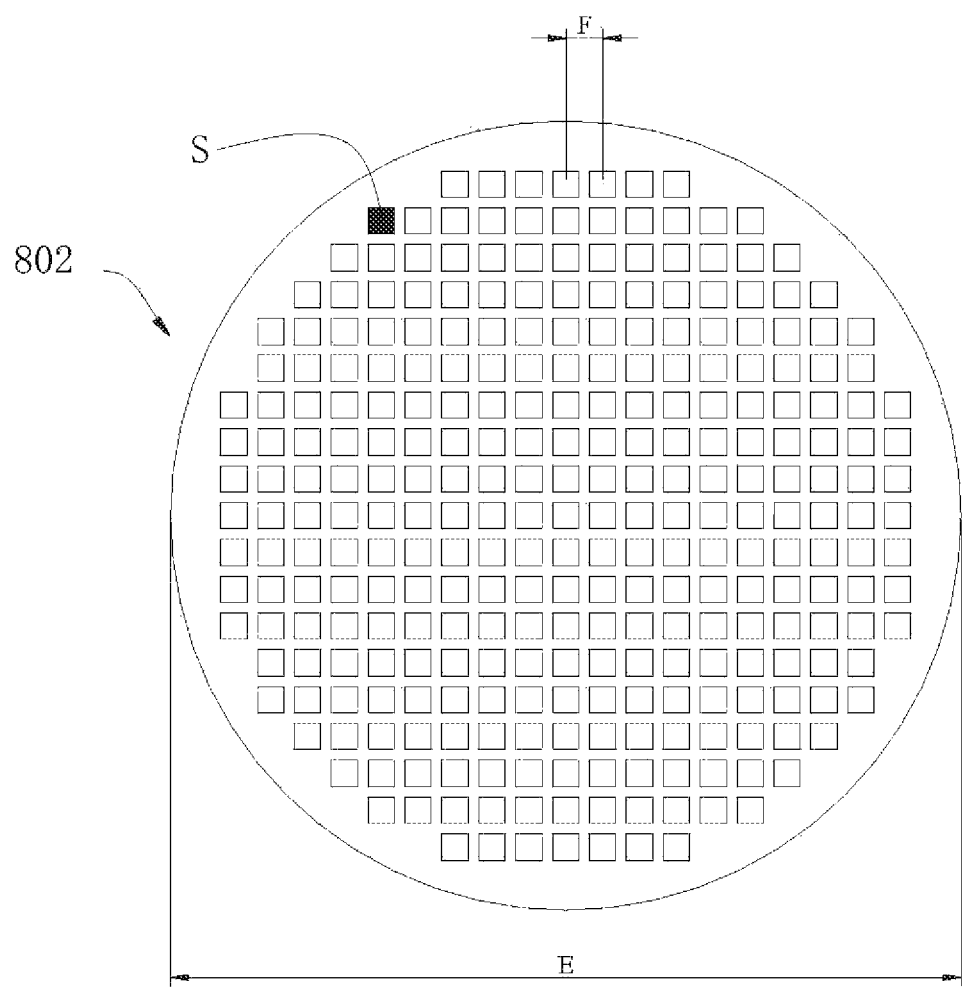
FIG. 18 is a schematic plan view of the activated carbon module according to an embodiment of the present application.

Please refer to FIGS. 17 and 18. In some embodiments, the activated carbon module 802 is a cylinder, the thickness D of the activated carbon module 802 is 38-45 mm, and the diameter E is 145-150 mm; and/or the cross-sectional area S of each filter hole 8022 is 20-30 mm$^2$, and the center distance F of two adjacent filter holes 8022 is 5-8 mm.

Please note that there are three cases about 'The thickness D of the activated carbon module 802 is 38-45 mm and the diameter E is 145-150 mm; and/or the cross-sectional area S of each filter hole 8022 is 20-30 mm$^2$, and the center distance F of two adjacent filter holes 8022 is 5-8 mm.':

In the first case, the thickness D of the activated carbon module 802 is 38-45 mm, and the diameter E is 145-150 mm;

In the second case, the cross-sectional area S of each filter hole 8022 is 20-30 mm$^2$, and the center distance F of two adjacent filter holes 8022 is 5-8 mm;

In the third case, the thickness D of the activated carbon module 802 is 38-45 mm, the diameter E is 145-150 mm, and the cross-sectional area S of each filter hole 8022 is 20-30 mm$^2$, and the center distance F between two adjacent filter holes 8022 is 5-8 mm.

In one example, the thickness D of the activated carbon module 802 is 38 mm and the diameter E is 145 mm; in another example, the thickness D of the activated carbon module 802 is 45 mm and the diameter E is 150 mm; in yet another example, the thickness D of the activated carbon module 802 is 41 mm and the diameter E is 147 mm.

In one example, the cross-sectional area S of each filter hole 8022 is 20 mm$^2$, and the center distance F of two adjacent filter holes 8022 is 5 mm; in another example, the cross-sectional area S of each filter hole 8022 is 30 mm$^2$, and the center distance F of two adjacent filter holes 8022 is 8 mm; in yet another example, the cross-sectional area S of each filter hole 8022 is 25 mm$^2$, and the center distance F of two adjacent filter holes 8022 is 6.5 mm.

In some embodiments, the purification housing 10 includes a cylinder 11, an upper cover element 14 disposed on an upper end of the cylinder 11, and a lower cover element 16 disposed on a lower end of the cylinder 11. The upper cover element 14 is used to connect components in downstream of the air purification module 100 in the air purifier 1000, and the lower cover element 16 is used to connect components in upstream of the air purification module 100 in the air purifier 1000.

Please note that "upstream" and "downstream" here are related to the direction of air flow in the air purifier 1000. Generally speaking, the air in the air purifier 1000 flows from the bottom to the top. Therefore, the upstream components are located below the air purification module 100 in a spatial position, and the downstream components are located above the air purification module 100 in a spatial position.

Referring to FIGS. 2 and 3, the upper cover element 14 includes an upper cover plate 141 and an upper mounting ring 144 extending from the upper cover plate 141 in a direction away from the cylinder 11. The upper cover plate 141 is formed an upper grille structure 1412 that communicates with the purification air duct 12. The upper mounting ring 144 surrounds the upper grille structure 1412 to form a purification air outlet 124. The activated carbon purification unit 80 is disposed in the upper mounting ring 144. The lower cover element 16 includes a lower cover plate 161 and a lower mounting ring 164 extending from the lower cover plate 161 in a direction away from the cylinder 11. The lower cover plate 161 is formed with a lower grill structure 1612, and the lower mounting ring 164 surrounds the lower grill structure 1612 to form the purification air outlet 124.

The upper mounting ring 144 is used to connect the air purification module 100 and components in downstream of the air purification module 100. The lower grille structure 1612 is used to filter excessively large soot particles, so as to prevent excessively large soot particles from entering the air purification module 100 and affecting the service life of the air purification module 100.

Furthermore, the lower grille structure 1612 can cooperate with the fan 200 to divide part of the soot particles smaller, thereby improving the purification efficiency of the air purification module 100. The lower mounting ring 164 is used to connect the air purification module 100 and components in upstream of the air purification module 100.

Specifically, the upper cover element 14 is used to connect components such as the exhaust pipe of the air purifier 1000, and the lower cover element 16 is used to connect the air purification module 100 and the body of the air purifier 1000.

Furthermore, the activated carbon purification unit 80 includes a fixing ring 804, the activated carbon module 802 is fixed in the fixing ring 804, and the activated carbon purification unit 80 is fixed in the upper mounting ring 144 by the fixing ring 804. In this way, the activated carbon purification unit 80 is fixed.

In some embodiments, the air purification module 100 includes a high voltage transformer 50. The high voltage transformer 50 is used to convert the effective value of the standard voltage 220V, which is most commonly used by residents, into a high voltage to supply for the the air purification module 100. For example, the high voltage transformer 50 may achieve the purpose of boosting by changing the turns ratio of the inductor coils.

In some embodiments, the air purification module 100 includes a power supply device 500 fixed on the outside of the purification housing 10, and the power supply device 500 is used to supply voltage to the multi-turn coils 24.

In some embodiments, the power supply device 500 includes a switch 60 and a switch box cover 70, and a button 62 of the switch 60 is exposed from the switch box cover 70. The user can control the opening and closing of the air purification module 100 through the button 62 of the switch 60. The switch box cover 70 encapsulates most of the switch 60 and exposes only the button 62, which is beneficial to the regularity and beauty of the air purification module 100.

In some embodiments, the switch 60 can adjust the power of the air purification module 100. The user can select a lower power when the lampblack is less and a higher power when the lampblack is more, so that it is convenient for the user to control the air purification module 100.

In some embodiments, the main switch of the air purifier 1000 and the switch 60 of the air purification module 100 are arranged together, so that it can be conveniently used by users.

In some embodiments, the main switch of the air purifier 1000 can adjust the power of the air purifier 1000. The user can select a lower power when the lampblack is less, and a higher power when the lampblack is more. Thereby, it is convenient for the user to control the air purifier 1000.

In some embodiments, the power supply device 500 includes a power socket 300, and the power socket 300 is used to connect the air purifier 1000 to a home circuit so as to power the air purifier 1000.

Generally, the fan 200 is disposed in the air duct 401 of the housing 400 of the air purifier 1000, and is closer to the stove than the air purification module 100. The air purifier 1000 is provided with an air inlet 402, and the air purifier 1000 is installed above the stove. When the user is cooking on the stove, the air purifier 1000 can be turned on to make the fan 200 running.

During the running of the fan 200, the lampblack generated during the cooking can be sucked into the air duct 401 of the air purifier 1000 through the air inlet 402, and then the lampblack is discharged to the purification air duct 12 of the air purification module 100 to make the air purification module 100 purifies and discharges the purified air. In addition, the fan 200 can also divide the soot particles into smaller pieces, so that the soot particles can be more easily processed in the air purification module 100.

In order to improve the service life of the air purifier 1000, a filter may be provided at the air inlet 402. The filter can filter the lampblack with large particles to prevent the lampblack with large particles from directly entering the air purifier 1000 and affecting the normal operation of the air purifier 1000.

In some embodiments, the air duct 401 includes an air outlet 403 provided indoors, and the fan 200 is used for sucking air from the air inlet 402 during operation and making the air pass through the ozone generation device 20 and the activated carbon purification unit 80, and then the purified air is discharged from the air outlet 403 into indoors.

In some examples, the exhaust direction of the air outlet 403 is directed upward; or the exhaust direction of the air outlet 403 is toward a side that the air purifier is located; or the purified air is discharged into a cupboard by the air outlet 403.

When the air outlet 403 discharges the purified air into the cupboard, the air can dry the utensils in the cupboard and get a double advantage.

Of course, the exhaust direction of the air outlet 403 may not be limited to the above three examples. In addition, one air outlet 403 may be provided, or multiple air outlets 403 may be provided. The exhaust direction and number of the air outlet 403 are not limited herein.

The air purifier 1000 includes an air purification module 100 provided above the fan 200, the housing 400 includes a purification housing 10, the air duct 401 includes a purification air duct 401, and the ozone generation device 20 and the activated carbon purification unit 80 are both disposed in the purification air duct 401. As such, the air purifier 1000 is modularized.

In summary, an air purifier 1000 provided by the present application includes a housing 400 formed with the air duct 401, an ozone generation device 20, an activated carbon purification unit 80, and a fan 200 provided in the air duct 401. An air outlet 403 is provided indoors. The ozone generation device 20 and the activated carbon purification unit 80 are arranged in the air duct 401 along the direction of the air inlet 402 to the air outlet 403. The ozone generation device 20 is used to generate ozone. The fan 200 is used to suck air from the air inlet 402 during operation and let the air pass through the ozone generation device 20 and the activated carbon purification unit 80 to be discharged from the air outlet 403 into the room.

The air purifier 1000 according to the embodiment of the present application purifies the air through the ozone generation device 20 and the activated carbon purification unit 80, so that the air purifier 1000 has a good capacity to purify the air, thereby the purified lampblack gas can be directly discharged into the room, which not only plays a role in lampblack gas purification, but also benefits indoor air circulation, environmental protection and energy saving.

It can be understood that at this time, the air purifier 1000 can not only serve as an air purifier to suck, purify the indoor air and discharge the purified air to the room for recycling, but also serve as a kitchen ventilator to remove the lampblack during cooking.

In the description of this specification, the description with reference to the terms "one embodiment", "some embodiments", "exemplary embodiments", "examples", "specific examples", or "some examples" and the like means that in combination with specific features, structures, materials, or characteristics described in the embodiments or examples are included in at least one embodiment or example of the present application. In this specification, the schematic expressions of the above terms do not necessarily refer to the same implementation or example. Furthermore, the particular features, structures, materials, or characteristics described may be combined in any suitable manner in any one or more implementations or examples.

Although the embodiments of the present application have been shown and described, those of ordinary skill in the art can understand that various changes, modifications, replacements and variations can be made to these embodiments without departing from the principles and spirit of the present application. The scope of the application is defined by the claims and their equivalents.

What is claimed is:

1. An air purifier, comprising:
   a housing formed with an air duct, the air duct comprising an air inlet and an air outlet, and the air outlet is disposed indoors;
   an ozone generation device configured to generate ozone and an activated carbon purification unit, the ozone generation device and the activated carbon purification unit being provided in the air duct along a direction from the air inlet to the air outlet; and
   a fan provided in the air duct, the fan is configured for sucking air from the air inlet during operation and allowing the air to pass through the ozone generation device and the activated carbon purification unit to be discharged from the air outlet into a room;
   the ozone generation device comprises:
   a frame; and
   multi-turn coils wound around the frame, wherein the multi-turn coils are arranged at intervals, at least two turns of the coils are used to ionize air to form ozone after an operating voltage is applied.

2. The air purifier according to claim 1, wherein an exhaust direction of the air outlet is directed upward; or the exhaust direction of the air outlet is toward a side that the air purifier is located; or a purified air is discharged into a cupboard by the air outlet.

3. The air purifier according to claim 1, wherein the air purifier comprises an air purification module disposed above the fan, the air purification module comprises a purification housing, the ozone generation device, and the activated carbon purification unit; wherein the purification housing is formed with a purification air duct, the purification air duct is formed with a purification air inlet and a purification air outlet, the housing comprises the purification housing, and the air duct comprises the purification air duct, the ozone generation device and the activated carbon purification unit are both disposed in the purification air duct.

4. The air purifier according to claim 3, wherein the activated carbon purification unit comprises an activated carbon module, the activated carbon module is formed with a plurality of filter holes communicating with the purification air inlet and the purification air outlet, and the plurality of filter holes are arranged in an array.

5. The air purifier according to claim 4, wherein the purification housing comprises:
   a cylinder;
   a lower cover element provided at a lower end of the cylinder, the lower cover element being formed with a lower grille structure communicating with the purification air duct; and
   an upper cover element provided at an upper end of the cylinder, the upper cover element comprises an upper cover plate and an upper mounting ring extending from the upper cover plate in a direction away from the cylinder, the upper cover plate is formed with an upper grille structure communicating with the purification air duct, the upper mounting ring surrounds the upper grille structure to form the purification air outlet, and the activated carbon purification unit is disposed in the upper mounting ring.

6. The air purifier according to claim 5, wherein the activated carbon purification unit comprises a fixed ring, the activated carbon module is fixed in the fixing ring, and the activated carbon purification unit is fixed in the upper mounting ring through the fixing ring.

7. The air purifier according to claim 5, wherein the lower cover element comprises a lower cover plate and a lower mounting ring extending from the lower cover plate in a direction away from the cylinder, the lower cover plate is formed with the lower grille structure, and the lower mounting ring surrounds the lower grille structure to form the purification air inlet.

8. The air purifier according to claim 1, wherein the frame comprises:
   two polar plates, wherein the two polar plates are set opposite to each other and at intervals; and
   a plurality of connection posts connected to the two polar plates and arranged at intervals, and the multi-turn coils are wound around the plurality of connection posts and arranged at intervals along an axial direction of the connection posts.

9. The air purifier according to claim 1, wherein coils to which a low potential is applied and coils to which a high potential is applied are alternately distributed in an arrangement direction of the multi-turn coils, wherein the low potential is 0V and the high potential is 3000-3500V.

* * * * *